United States Patent
Foreman

(10) Patent No.: US 11,571,570 B2
(45) Date of Patent: Feb. 7, 2023

(54) POWER CONTROL CIRCUIT FOR STERILIZED DEVICES, AND ASSOCIATED SYSTEMS AND METHODS

(71) Applicant: Nevro Corp., Redwood City, CA (US)

(72) Inventor: Bret Foreman, Redwood City, CA (US)

(73) Assignee: Nevro Corp., Redwood City, CA (US)

(*) Notice: Subject to any disclaimer, the term of this patent is extended or adjusted under 35 U.S.C. 154(b) by 67 days.

(21) Appl. No.: 17/160,223

(22) Filed: Jan. 27, 2021

(65) Prior Publication Data
US 2021/0146134 A1     May 20, 2021

Related U.S. Application Data

(62) Division of application No. 16/264,315, filed on Jan. 31, 2019, now Pat. No. 10,933,238.

(51) Int. Cl.
*A61N 1/36* (2006.01)
*G05F 1/56* (2006.01)

(52) U.S. Cl.
CPC ........... *A61N 1/36034* (2017.08); *G05F 1/56* (2013.01)

(58) Field of Classification Search
CPC ...... A61N 1/36034; A61N 2001/37294; A61N 1/3603; A61N 1/37241; A61N 1/36017; G05F 1/56
USPC ........................................................ 607/59
See application file for complete search history.

(56) References Cited

U.S. PATENT DOCUMENTS

| | | |
|---|---|---|
| 3,871,382 A | 3/1975 | Mann |
| 4,071,032 A | 1/1978 | Schulman |
| 4,082,097 A | 4/1978 | Mann et al. |
| D250,719 S | 1/1979 | Jacobson et al. |
| 4,197,850 A | 4/1980 | Schulman et al. |
| 4,230,121 A | 10/1980 | Stanton |
| 4,441,498 A | 4/1984 | Nordling |
| D280,930 S | 10/1985 | Speicher et al. |

(Continued)

FOREIGN PATENT DOCUMENTS

| | | |
|---|---|---|
| EP | 0754437 | 1/1997 |
| EP | 1610437 | 12/2005 |

(Continued)

OTHER PUBLICATIONS

Received STIC search report from EIC 2800 searcher Michael Giles for claim 22 on Feb. 10, 2022. (Year: 2022).*

(Continued)

*Primary Examiner* — Shawki S Ismail
*Assistant Examiner* — Htet Z Kyaw
(74) *Attorney, Agent, or Firm* — Perkins Coie LLP

(57) ABSTRACT

A power control circuit for use with devices that will be placed in a flammable sterilizing gas includes a bi-stable switch that is configured to produce an output to place the circuitry of a connected device in a run state or a sleep state. The bi-stable switch controls one or more transistors to drain energy from energy storage devices in the circuitry of the connected device to a level below an ignition level of a sterilizing gas. A remotely actuatable switch can be actuated from outside of a packaging in which the power control circuit is placed to cause the bi-stable switch to produce an output that puts the circuitry in the run state without removing the power control circuit from the packaging.

20 Claims, 4 Drawing Sheets

(56) References Cited

U.S. PATENT DOCUMENTS

| | | | |
|---|---|---|---|
| 4,556,063 A * | 12/1985 | Thompson | A61N 1/37211 128/903 |
| 4,632,117 A | 12/1986 | James | |
| 4,636,706 A | 1/1987 | Bowman et al. | |
| 4,642,479 A * | 2/1987 | Lombardi | G06F 1/26 333/24 R |
| 4,890,616 A | 1/1990 | Pinckaers | |
| 5,065,083 A | 11/1991 | Owens | |
| 5,144,946 A | 9/1992 | Weinberg et al. | |
| D337,820 S | 7/1993 | Hooper et al. | |
| 5,279,292 A | 1/1994 | Baumann et al. | |
| D343,901 S | 2/1994 | Anderson | |
| 5,591,212 A | 1/1997 | Keimel | |
| 5,733,313 A | 3/1998 | Barreras, Sr. et al. | |
| 5,755,743 A | 5/1998 | Volz et al. | |
| 5,769,877 A | 6/1998 | Barreras, Sr. | |
| 5,782,880 A | 7/1998 | Lahtinen | |
| 5,807,397 A | 9/1998 | Barreras | |
| 5,928,272 A | 7/1999 | Adkins et al. | |
| 5,929,615 A * | 7/1999 | D'Angelo | G05F 1/618 323/224 |
| 5,954,758 A | 9/1999 | Peckham et al. | |
| 6,026,328 A | 2/2000 | Peckham et al. | |
| 6,076,018 A | 6/2000 | Sturman et al. | |
| 6,115,634 A | 9/2000 | Donders et al. | |
| 6,167,303 A | 12/2000 | Thompson | |
| 6,185,452 B1 | 2/2001 | Schulman et al. | |
| 6,185,454 B1 | 2/2001 | Thompson | |
| 6,223,080 B1 | 4/2001 | Thompson | |
| 6,236,888 B1 | 5/2001 | Thompson | |
| 6,323,603 B1 | 11/2001 | Persson | |
| 6,324,426 B1 | 11/2001 | Thompson | |
| 6,387,332 B1 | 5/2002 | Dickinson | |
| 6,434,425 B1 | 8/2002 | Thompson | |
| 6,453,198 B1 | 9/2002 | Torgerson et al. | |
| 6,472,991 B1 | 10/2002 | Schulman et al. | |
| 6,496,729 B2 | 12/2002 | Thompson | |
| 6,553,263 B1 | 4/2003 | Meadows et al. | |
| D478,990 S | 8/2003 | Kroll | |
| 6,650,943 B1 | 11/2003 | Whitehurst et al. | |
| 6,712,772 B2 | 3/2004 | Cohen et al. | |
| 6,757,561 B2 | 6/2004 | Rubin et al. | |
| 6,812,708 B2 | 11/2004 | Bristol | |
| 6,871,099 B1 | 3/2005 | Whitehurst et al. | |
| 6,909,915 B2 | 6/2005 | Greatbatch | |
| 7,027,860 B2 | 4/2006 | Bruninga et al. | |
| 7,054,689 B1 | 5/2006 | Whitehurst et al. | |
| D523,144 S | 6/2006 | Wenger et al. | |
| 7,120,499 B2 | 10/2006 | Thrope et al. | |
| 7,127,288 B2 | 10/2006 | Sturman et al. | |
| 7,142,923 B2 | 11/2006 | North et al. | |
| 7,167,749 B2 | 1/2007 | Biggs et al. | |
| 7,167,756 B1 | 1/2007 | Torgerson et al. | |
| 7,177,703 B2 | 2/2007 | Boveja et al. | |
| 7,184,836 B1 | 2/2007 | Meadows et al. | |
| 7,209,792 B1 | 4/2007 | Parramon et al. | |
| 7,254,449 B2 | 8/2007 | Karunasiri | |
| 7,263,405 B2 | 8/2007 | Boveja et al. | |
| D559,987 S | 1/2008 | Strother et al. | |
| 7,330,762 B2 | 2/2008 | Boveja et al. | |
| 7,337,010 B2 | 2/2008 | Howard et al. | |
| 7,437,193 B2 | 10/2008 | Parramon et al. | |
| 7,444,184 B2 | 10/2008 | Boveja et al. | |
| 7,489,968 B1 | 2/2009 | Alexander | |
| 7,496,404 B2 | 2/2009 | Meadows et al. | |
| 7,571,002 B2 | 8/2009 | Thrope et al. | |
| 7,606,622 B2 | 10/2009 | Reeve | |
| 7,616,990 B2 | 11/2009 | Chavan et al. | |
| 7,620,454 B2 | 11/2009 | Dinsmoor et al. | |
| 7,636,602 B2 | 12/2009 | Baru Fassio et al. | |
| 7,641,992 B2 | 1/2010 | Howard et al. | |
| 7,650,191 B1 | 1/2010 | Lim et al. | |
| D610,261 S | 2/2010 | Strother et al. | |
| 7,682,745 B2 | 3/2010 | Howard et al. | |
| 7,697,984 B2 | 4/2010 | Hill et al. | |
| 7,769,442 B2 | 8/2010 | Shafer | |
| 7,769,462 B2 | 8/2010 | Meadows et al. | |
| 7,801,601 B2 | 9/2010 | Maschino et al. | |
| 7,801,615 B2 | 9/2010 | Meadows et al. | |
| 7,805,189 B2 | 9/2010 | Stein | |
| 7,818,068 B2 | 10/2010 | Meadows et al. | |
| 7,848,812 B2 | 12/2010 | Crowley | |
| 7,865,245 B2 | 1/2011 | Torgerson et al. | |
| 7,879,495 B2 | 2/2011 | Howard et al. | |
| 7,894,905 B2 | 2/2011 | Pless | |
| 7,916,013 B2 | 3/2011 | Stevenson | |
| 7,941,220 B2 | 5/2011 | Tobacman | |
| 8,128,600 B2 | 3/2012 | Gill | |
| 8,150,521 B2 | 4/2012 | Crowley | |
| 8,190,259 B1 | 5/2012 | Smith et al. | |
| D663,035 S | 7/2012 | Smith | |
| D665,086 S | 8/2012 | Smith | |
| D665,087 S | 8/2012 | Smith | |
| 8,355,797 B2 | 1/2013 | Caparso et al. | |
| 8,571,679 B2 | 10/2013 | Parramon et al. | |
| 8,583,954 B2 * | 11/2013 | Dinsmoor | G06F 1/30 713/340 |
| 8,929,986 B2 | 1/2015 | Parker | |
| 8,965,514 B2 | 2/2015 | Bikson et al. | |
| 9,013,938 B1 | 4/2015 | Moscaluk et al. | |
| 9,061,152 B2 | 6/2015 | Shi et al. | |
| 9,192,769 B2 | 11/2015 | Donofrio et al. | |
| 9,227,076 B2 | 1/2016 | Sharma et al. | |
| 9,409,020 B2 | 8/2016 | Parker | |
| 9,466,997 B2 | 10/2016 | Silva | |
| 9,533,164 B2 | 1/2017 | Erickson | |
| 9,884,198 B2 | 2/2018 | Parker et al. | |
| 10,420,935 B2 | 9/2019 | Illegems | |
| 10,933,238 B2 | 3/2021 | Foreman | |
| 2002/0035385 A1 | 3/2002 | Deziz | |
| 2002/0068956 A1 | 6/2002 | Bloemer et al. | |
| 2002/0107554 A1 | 8/2002 | Biggs et al. | |
| 2002/0193844 A1 | 12/2002 | Michelson et al. | |
| 2003/0107349 A1 | 6/2003 | Haydock et al. | |
| 2003/0110058 A1 | 6/2003 | Adie | |
| 2003/0114899 A1 | 6/2003 | Woods et al. | |
| 2003/0135241 A1 | 7/2003 | Leonard et al. | |
| 2003/0149459 A1 * | 8/2003 | Von Arx | A61N 1/37276 607/60 |
| 2003/0191504 A1 | 10/2003 | Meadows et al. | |
| 2003/0195581 A1 | 10/2003 | Meadows et al. | |
| 2003/0204222 A1 | 10/2003 | Leinders et al. | |
| 2003/0208244 A1 | 11/2003 | Stein et al. | |
| 2004/0034393 A1 | 2/2004 | Hansen et al. | |
| 2004/0098060 A1 | 5/2004 | Ternes | |
| 2004/0215287 A1 | 10/2004 | Swoyer et al. | |
| 2004/0225333 A1 | 11/2004 | Greatbatch | |
| 2005/0025480 A1 | 2/2005 | Yeh | |
| 2005/0075695 A1 | 4/2005 | Schommer et al. | |
| 2005/0131467 A1 | 6/2005 | Boveja | |
| 2005/0131483 A1 | 6/2005 | Zhao | |
| 2005/0131486 A1 | 6/2005 | Boveja et al. | |
| 2005/0131487 A1 | 6/2005 | Boveja et al. | |
| 2005/0137644 A1 | 6/2005 | Boveja et al. | |
| 2005/0143787 A1 | 6/2005 | Boveja et al. | |
| 2005/0149146 A1 | 7/2005 | Boveja et al. | |
| 2005/0154425 A1 | 7/2005 | Boveja et al. | |
| 2005/0154426 A1 | 7/2005 | Boveja et al. | |
| 2005/0165458 A1 | 7/2005 | Boveja et al. | |
| 2005/0174098 A1 | 8/2005 | Watanabe | |
| 2005/0178372 A1 | 8/2005 | Kesler et al. | |
| 2005/0187590 A1 | 8/2005 | Boveja et al. | |
| 2005/0197678 A1 | 9/2005 | Boveja et al. | |
| 2005/0203583 A1 | 9/2005 | Twetan et al. | |
| 2005/0203584 A1 | 9/2005 | Twetan et al. | |
| 2005/0216070 A1 | 9/2005 | Boveja et al. | |
| 2005/0218726 A1 * | 10/2005 | Jenson | H01M 10/4257 429/162 |
| 2005/0266301 A1 | 12/2005 | Smith et al. | |
| 2005/0267546 A1 | 12/2005 | Parramon et al. | |
| 2006/0004422 A1 | 1/2006 | De Ridder | |
| 2006/0122655 A1 | 6/2006 | Greatbatch et al. | |
| 2006/0190060 A1 * | 8/2006 | Greeninger | A61N 1/3787 607/34 |

(56) References Cited

U.S. PATENT DOCUMENTS

| | | |
|---|---|---|
| 2006/0224208 A1 | 10/2006 | Naviaux |
| 2007/0060955 A1 | 3/2007 | Strother et al. |
| 2007/0060968 A1 | 3/2007 | Strother et al. |
| 2007/0060980 A1 | 3/2007 | Strother et al. |
| 2007/0111587 A1 | 5/2007 | Ries et al. |
| 2007/0129768 A1 | 6/2007 | He |
| 2007/0142728 A1* | 6/2007 | Penner .............. A61B 5/0031 600/561 |
| 2007/0210759 A1 | 9/2007 | Sano |
| 2007/0213783 A1 | 9/2007 | Pless |
| 2007/0265489 A1 | 11/2007 | Fowler et al. |
| 2007/0270916 A1 | 11/2007 | Fischell et al. |
| 2008/0015644 A1 | 1/2008 | Julian |
| 2008/0039904 A1 | 2/2008 | Bulkes et al. |
| 2008/0058901 A1 | 3/2008 | Ternes et al. |
| 2008/0065182 A1 | 3/2008 | Strother et al. |
| 2008/0077184 A1 | 3/2008 | Denker et al. |
| 2008/0097554 A1 | 4/2008 | Payne et al. |
| 2008/0125833 A1 | 5/2008 | Bradley et al. |
| 2008/0129225 A1 | 6/2008 | Yamamoto et al. |
| 2008/0132926 A1 | 6/2008 | Eichmann et al. |
| 2008/0156333 A1 | 7/2008 | Galpern et al. |
| 2008/0216846 A1 | 9/2008 | Levin |
| 2008/0243210 A1* | 10/2008 | Doron .............. A61N 1/37217 607/60 |
| 2008/0255631 A1 | 10/2008 | Sjostedt et al. |
| 2008/0262563 A1 | 10/2008 | Sjostedt |
| 2008/0294219 A1 | 11/2008 | Osypka et al. |
| 2008/0319441 A1 | 12/2008 | Seid |
| 2009/0012576 A1 | 1/2009 | Erbstoeszer et al. |
| 2009/0017700 A1 | 1/2009 | Zart et al. |
| 2009/0018600 A1 | 1/2009 | Deininger et al. |
| 2009/0018607 A1 | 1/2009 | Crowley et al. |
| 2009/0048643 A1 | 2/2009 | Erickson |
| 2009/0132010 A1 | 5/2009 | Kronberg |
| 2009/0157142 A1 | 6/2009 | Cauller |
| 2009/0204119 A1 | 8/2009 | Bleich et al. |
| 2009/0204173 A1 | 8/2009 | Fang et al. |
| 2009/0210029 A1 | 8/2009 | Tsui |
| 2009/0228074 A1 | 9/2009 | Edgell et al. |
| 2009/0248094 A1 | 10/2009 | McDonald |
| 2009/0248118 A1 | 10/2009 | Bradley et al. |
| 2009/0270948 A1 | 10/2009 | Nghiem et al. |
| 2009/0281596 A1 | 11/2009 | King et al. |
| 2009/0281599 A1 | 11/2009 | Thacker et al. |
| 2009/0287946 A1* | 11/2009 | Lin .............. G06F 1/3265 713/323 |
| 2010/0004654 A1 | 1/2010 | Schmitz et al. |
| 2010/0010567 A1 | 1/2010 | Deem et al. |
| 2010/0038132 A1 | 2/2010 | Kinney et al. |
| 2010/0049275 A1 | 2/2010 | Chavan et al. |
| 2010/0094115 A1 | 4/2010 | Pond, Jr. et al. |
| 2010/0094231 A1 | 4/2010 | Bleich et al. |
| 2010/0106223 A1 | 4/2010 | Grevious et al. |
| 2010/0137943 A1 | 6/2010 | Zhu |
| 2010/0137944 A1 | 6/2010 | Zhu |
| 2010/0144281 A1 | 6/2010 | Kim et al. |
| 2010/0144283 A1 | 6/2010 | Curcio et al. |
| 2010/0168818 A1 | 7/2010 | Barror et al. |
| 2010/0233896 A1 | 9/2010 | Dilmaghanian |
| 2010/0274314 A1 | 10/2010 | Alataris et al. |
| 2010/0274317 A1 | 10/2010 | Parker et al. |
| 2010/0305631 A1 | 12/2010 | Bradley et al. |
| 2010/0305663 A1 | 12/2010 | Aghassian |
| 2010/0324570 A1 | 12/2010 | Rooney et al. |
| 2011/0054583 A1 | 3/2011 | Litt et al. |
| 2011/0060282 A1 | 3/2011 | Dogwiler et al. |
| 2011/0071593 A1 | 3/2011 | Parker et al. |
| 2011/0112601 A1 | 5/2011 | Meadows et al. |
| 2011/0112609 A1 | 5/2011 | Peterson |
| 2011/0112610 A1 | 5/2011 | Rahman et al. |
| 2011/0118661 A1 | 5/2011 | Pless et al. |
| 2011/0144468 A1 | 6/2011 | Boggs et al. |
| 2011/0160804 A1* | 6/2011 | Penner .............. A61B 5/0031 607/62 |
| 2011/0224710 A1 | 9/2011 | Bleich |
| 2011/0245708 A1 | 10/2011 | Finkel et al. |
| 2011/0270363 A1 | 11/2011 | Schramm |
| 2012/0066534 A1* | 3/2012 | Dinsmoor ............... G06F 1/30 713/340 |
| 2012/0095744 A1 | 4/2012 | Rahman |
| 2012/0101551 A1 | 4/2012 | Aghassian et al. |
| 2012/0239108 A1 | 9/2012 | Foutz |
| 2012/0253440 A1 | 10/2012 | Grohmann |
| 2012/0315798 A1 | 12/2012 | Poon et al. |
| 2013/0035740 A1 | 2/2013 | Sharma |
| 2013/0066399 A1 | 3/2013 | Min |
| 2013/0066411 A1 | 3/2013 | Thacker et al. |
| 2013/0110058 A1* | 5/2013 | Adie ..................... A61M 1/90 604/319 |
| 2013/0238048 A1 | 9/2013 | Almendinger et al. |
| 2014/0121787 A1* | 5/2014 | Yamazaki ............ H02M 3/156 700/19 |
| 2014/0217291 A1 | 8/2014 | Deutscher |
| 2014/0277268 A1 | 9/2014 | Lee |
| 2015/0005842 A1 | 1/2015 | Lee |
| 2015/0039047 A1 | 2/2015 | Parker |
| 2015/0039048 A1 | 2/2015 | Woods |
| 2015/0088227 A1 | 3/2015 | Shishilla et al. |
| 2016/0114171 A1 | 4/2016 | Parker |
| 2016/0124455 A1 | 5/2016 | Sambucco et al. |
| 2016/0256696 A1 | 9/2016 | Sharma |
| 2017/0036023 A1 | 2/2017 | Parker |
| 2017/0202607 A1* | 7/2017 | Shelton, IV ....... A61B 18/1445 |
| 2018/0256892 A1 | 9/2018 | Wong |
| 2019/0341803 A1 | 11/2019 | Cook |
| 2021/0335285 A1* | 10/2021 | Liu ..................... H02J 7/0047 |

FOREIGN PATENT DOCUMENTS

| | | |
|---|---|---|
| EP | 2243510 | 10/2010 |
| JP | 2002090196 | 3/2002 |
| WO | WO-2008121110 | 10/2008 |
| WO | WO-2011094074 A1 | 8/2011 |
| WO | WO-2012054234 | 4/2012 |

OTHER PUBLICATIONS

Received STIC search report from EIC 2800 searcher Samir Patel for claim 31 on Feb. 17, 2022. (Year: 2022).*

Received STIC search report from EIC 2800 searcher Vaisali Koppolu for claim 35 on Feb. 15, 2022. (Year: 2022).*

Gainer et al., "Use of the Peripheral Nerve Stimulator and Standard, Unsheathed Needles in Performing Regional Nerve Blocks," CRNA: The Clinical Forum for Nurse Anesthetists, vol. 3, No. 4, Nov. 1992, 4 pages.

Holst et al., "Nervous Control of Pancreatic exocrine secretion in pigs," Acta, Physiol. Scan 1979, 105, 19 pages.

Huxely et al., "Excitation and Conduction in Nerve: Quantitative Analysis," Science, Sep. 11, 1964; 145: 1154-9.

International Search Report and Written Opinion for International Patent Application No. PCT/US2019/016153, Applicant: Nevro Corp., dated Oct. 21, 2019, 10 pages.

Klein, "Continuous Peripheral Nerve Blocks," Anesthesiology, vol. 103, No. 5, Nov. 2005, 3 pages.

Kumar et al., "Spinal Cord Stimulation in Treatment of Chronic Benign Pain: Challenges in Treatment Planning and Present Status, a 22-Year Experience," Neurosurgery, vol. 58, No. 3, Mar. 2006, 16 pages.

Linderoth et al., "Mechanisms of Spinal Cord Stimulation in Painful Syndromes: Role of Animal Models," Pain Medicine, vol. 7, No. S1, 2006, 13 pages.

Mediati, R.D., , "Mechanisms of Spinal Cord Stimulation," Florence, Oct. 2, 2002, 31 pages.

North et al., "Spinal Cord Stimulation for Axial Low Back Pain," Spine, vol. 30, No. 12, 2005, 7 pages.

North et al., "Spinal Cord Stimulation for Chronic, Intractable Pain: Experience over Two Decades," Neurosurgery, vol. 32, No. 2, Mar. 1993, 12 pages.

(56) References Cited

OTHER PUBLICATIONS

Paterson CA et al., "Determinants of Occurrence and Volume of Transpyloric Flow During Gastric Emptying of Liquids in Dogs: Importance of Vagal Input," Dig Dis Sci, 2000, 45: 1509-1516.
Vadalouca et al., "Therapeutic Management of Chronic Neuropathic Pain: An Examination of Pharmacologic Treatment," Annals New York Academy of Sciences, 2006, pp. 164-186.
Extended European Search Report for European Patent Application No. 19913183.0, Applicant: Nevro Corp., dated Jul. 28, 2022, 7 pages.

* cited by examiner

POWER CONTROL CIRCUIT FOR STERILIZED DEVICES, AND ASSOCIATED SYSTEMS AND METHODS

The present application is a divisional of U.S. patent application Ser. No. 16/264,315, filed on Jan. 31, 2019, which is incorporated herein by reference in its entirety.

TECHNICAL FIELD

The presently disclosed technology relates generally to electronic medical devices that are to be sterilized in flammable environments prior to use and, in particular, to sterilizable trial stimulators for use with implantable neurological stimulation systems.

BACKGROUND

Neurological stimulators have been developed to treat a variety of conditions such as pain, movement disorders, functional disorders, spasticity, cardiac disorders, and various other medical conditions. Implantable neurological stimulation systems generally have an implantable signal generator and one or more leads that deliver electrical pulses to neurological and/or muscle tissue. Often such devices have one or more electrodes that are inserted into the body near the target tissue to deliver the electrical pulses for therapeutic effect.

Once implanted, the signal generator is programmed to supply electrical pulses to the electrodes, which in turn modify the function of the patient's nervous system, such as by altering the patient's responsiveness to sensory stimuli and/or altering the patient's motor-circuit output. In spinal cord stimulation (SCS) therapy for the treatment of pain, the signal generator applies electrical pulses to the spinal cord via the electrodes that mask or otherwise alter the patient's sensation of pain.

In most cases, tests are performed to see if the patient notices an improvement from the application of the therapy pulses before a signal generator is implanted into the patient. Accordingly, an external trial stimulator is attached to the implanted electrodes and can be programmed to deliver electrical pulses with varying signal levels, frequencies, time durations etc. If the patient responds well after wearing the trial stimulator, the patient receives a more permanent implantable stimulator. The implantable stimulator can be programmed with the therapy regimen that was determined to be the most beneficial during the trial period. If necessary, the signal generator can be further programmed while implanted to fine tune the most beneficial therapy regimen.

DETAILED DESCRIPTION

The present technology is directed generally to power control circuits for selectively powering circuit components and, in some embodiments for selectively powering circuit components in sterilizable devices, and associated systems and methods. In some embodiments, the presently disclosed technologies are directed to systems and devices for discharging energy storage elements in a medical device that is to be placed in a flammable sterilizing gas after manufacture and prior to use. For example, a bi-stable switch can control one or more transistors to drain energy from an energy storage device to a level below an ignition level of a sterilizing gas. The bi-stable switch can be triggered to change states via a remotely actuatable switch from outside a sealed packaging in which the circuit is placed so as not to break the sealed package in the process of re-activating the medical device.

Definitions

Unless otherwise stated, the terms "about" and "approximately" refer to values within 10% of a stated value.

As used herein, the term "and/or," as in "A and/or B" refers to A alone, B alone and both A and B.

References to "some embodiments," "one embodiment," or the like, mean that the particular feature, function, structure or characteristic being described is included in at least one embodiment of the disclosed technology. Occurrences of such phrases in this specification do not necessarily all refer to the same embodiment. On the other hand, the embodiments referred to are not necessarily mutually exclusive. Elements described in the context of representative devices, systems and methods may be applied to other representative devices, systems and methods in a variety of suitable manners.

To the extent any materials incorporated herein by reference conflict with the present disclosure, the present disclosure controls.

As used herein, and unless otherwise noted, the terms "modulate," "modulation," "stimulate," and "stimulation" refer generally to signals that have an inhibitory, excitatory, and/or other effect on a target neural population. Accordingly, a spinal cord "stimulator" can have an inhibitory effect on certain neural populations.

System Overview

Figure 1:
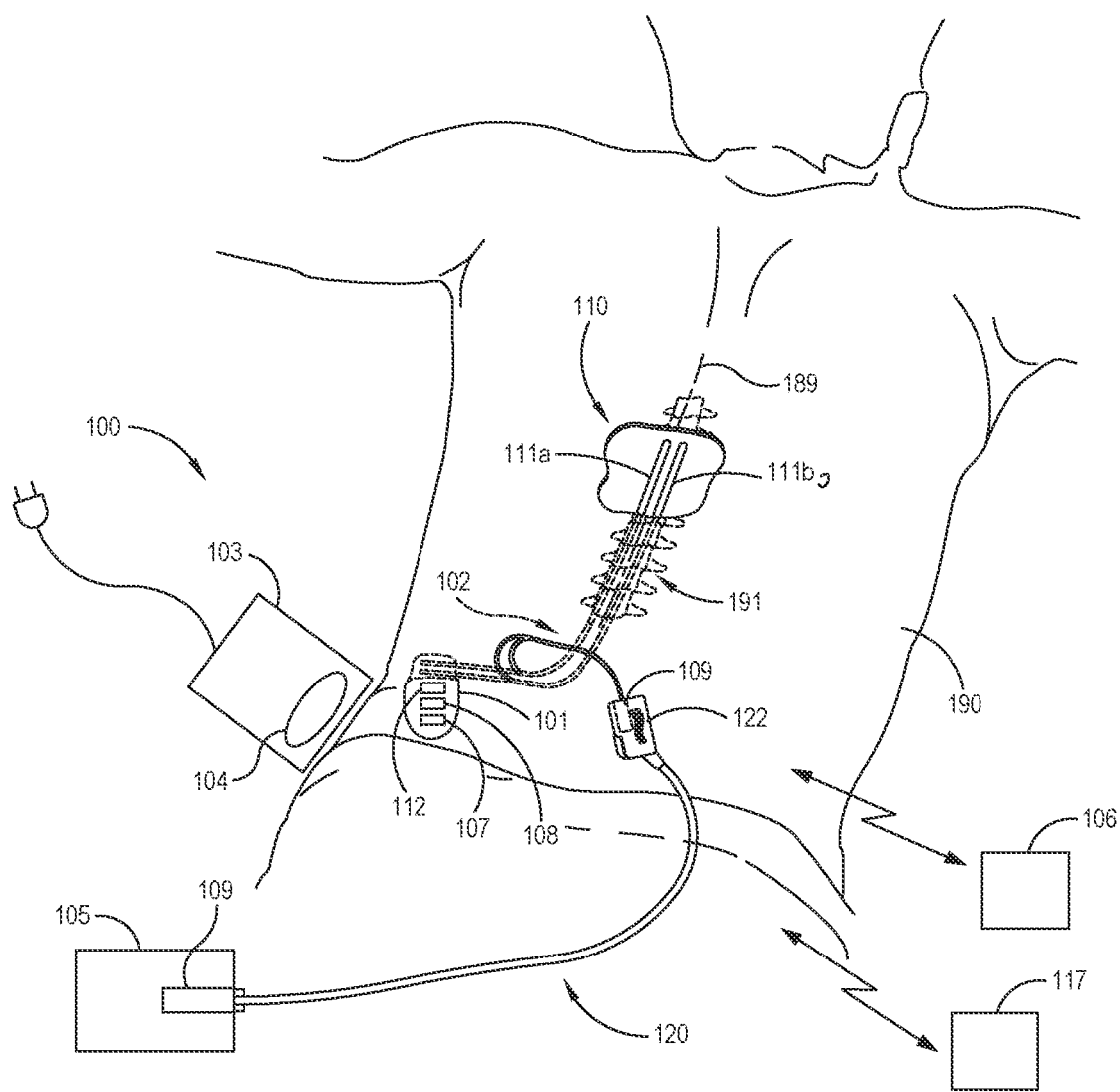
FIG. 1 is a partially schematic illustration of an implantable spinal cord modulation system positioned at a patient's spine to deliver therapeutic signals in accordance with some embodiments of the present technology.

FIG. 1 schematically illustrates a representative patient therapy system 100 for treating a patient's neurological disorders, arranged relative to the general anatomy of the patient's spinal column 191. The system 100 can include a signal generator 101 (e.g., an implanted or implantable pulse generator or IPG), which may be implanted subcutaneously within a patient 190 and coupled to one or more signal delivery elements or devices 110. The signal delivery elements or devices 110 may be implanted within the patient 190, at or off the patient's spinal cord midline 189. The signal delivery elements 110 carry features for delivering therapy to the patient 190 after implantation. The signal generator 101 can be connected directly to the signal delivery devices 110, or it can be coupled to the signal delivery devices 110 via a signal link, e.g., a lead extension 102. In some embodiments, the signal delivery devices 110 can include one or more elongated lead(s) or lead body or bodies 111 (identified individually as a first lead 111a and a second lead 111b). As used herein, the terms signal delivery device, signal delivery element, lead, and/or lead body include any of a number of suitable substrates and/or supporting members that carry electrodes/devices for providing therapy signals to the patient 190. For example, the lead or leads 111 can include one or more electrodes or electrical contacts that direct electrical signals into the patient's tissue, e.g., to provide for therapeutic relief. In some embodiments, the signal delivery elements 110 can include structures other than a lead body (e.g., a paddle) that also direct electrical signals and/or other types of signals to the patient 190, e.g., as disclosed in U.S. Patent Application Publication No. 2018/0256892, which is herein incorporated by reference in its entirety. For example, paddles may be more suitable for patients with spinal cord injuries that result in scarring or other tissue damage that impedes signal delivery from cylindrical leads.

In some embodiments, one signal delivery device may be implanted on one side of the spinal cord midline 189, and a second signal delivery device may be implanted on the other side of the spinal cord midline 189. For example, the first and second leads 111a, 111b shown in FIG. 1 may be positioned just off the spinal cord midline 189 (e.g., about 1 mm offset) in opposing lateral directions so that the two leads 111a, 111b are spaced apart from each other by about 2 mm. In some embodiments, the leads 111 may be implanted at a vertebral level ranging from, for example, about T4 to about T12. In some embodiments, one or more signal delivery devices can be implanted at other vertebral levels, e.g., as disclosed in U.S. Pat. No. 9,327,121, which is herein incorporated by reference in its entirety.

The signal generator 101 can provide signals (e.g., electrical signals) to the signal delivery elements 110 that excite and/or suppress target nerves. The signal generator 101 can include a machine-readable (e.g., computer-readable) or controller-readable medium (e.g. a memory circuit) containing instructions that are executable by a processor for generating suitable therapy signals. The signal generator 101 and/or other elements of the system 100 can include one or more processor(s) 107, memory unit(s) 108, and/or input/output device(s) 112. Accordingly, instructions for performing tasks such as providing modulation signals, setting battery charging and/or discharging parameters, and/or executing other associated functions can be stored on or in computer-readable media located at the signal generator 101 and/or other system components. Further, the signal generator 101 and/or other system components may include dedicated hardware for executing computer-executable instructions or configured logic circuitry such as FPGAs to perform any one or more methods, processes, and/or sub-processes described in the materials incorporated herein by reference. The dedicated hardware also serve as "means for" performing the methods, processes, and/or sub-processes described herein. The signal generator 101 can also include multiple portions, elements, and/or subsystems (e.g., for directing signals in accordance with multiple signal delivery parameters), carried in a single housing, as shown in FIG. 1, or in multiple housings.

The signal generator 101 can also receive and respond to an input signal received from one or more sources. The input signals can direct or influence the manner in which the therapy, charging, and/or process instructions are selected, executed, updated, and/or otherwise performed. The input signals can be received from one or more sensors (e.g., an input device 112 shown schematically in FIG. 1 for purposes of illustration) that are carried by the signal generator 101 and/or distributed outside the signal generator 101 (e.g., at other patient locations) while still communicating with the signal generator 101. The sensors and/or other input devices 112 can provide inputs that depend on or reflect a patient state (e.g., patient position, patient posture, and/or patient activity level), and/or inputs that are patient-independent (e.g., time). Still further details are included in U.S. Pat. No. 8,355,797, which is herein incorporated herein by reference in its entirety.

In some embodiments, the signal generator 101 and/or signal delivery devices 110 can obtain power to generate the therapy signals from an external power source 103. For example, the external power source 103 can by-pass an implanted signal generator and be used to generate a therapy signal directly at the signal delivery devices 110 (or via signal relay components). In some embodiments, the external power source 103 can transmit power to the implanted signal generator 101 and/or directly to the signal delivery devices 110 using electromagnetic induction (e.g., RF signals). For example, the external power source 103 can include an external coil 104 that communicates with a corresponding internal coil (not shown) within the implantable signal generator 101, signal delivery devices 110, and/or a power relay component (not shown). The external power source 103 can be portable for ease of use.

In some embodiments, the signal generator 101 can obtain the power to generate therapy signals from an internal power source, in addition to or in lieu of the external power source 103. For example, the implanted signal generator 101 can include a non-rechargeable battery or a rechargeable battery to provide such power. When the internal power source includes a rechargeable battery, the external power source 103 can be used to recharge the battery. The external power source 103 can in turn be recharged from a suitable power source (e.g., conventional wall power).

During at least some procedures, an external stimulator or trial stimulator 105 can be coupled to the signal delivery elements 110 during an initial procedure, prior to implanting the signal generator 101. For example, a practitioner (e.g., a physician and/or a company representative) can use the trial stimulator 105 to vary the modulation parameters provided to the signal delivery elements 110 in real time and select optimal or particularly efficacious parameters. These parameters can include the location from which the electrical signals are emitted, as well as the characteristics of the electrical signals provided to the signal delivery devices 110. In some embodiments, input is collected via the external stimulator or trial stimulator and can be used by the clinician to help determine what parameters to vary.

In a typical process, the practitioner uses a cable assembly 120 to temporarily connect the trial stimulator 105 to the signal delivery device 110. The practitioner can test the efficacy of the signal delivery devices 110 in an initial position. The practitioner can then disconnect the cable assembly 120 (e.g., at a connector 122), reposition the signal delivery devices 110, and reapply the electrical signals. This process can be performed iteratively until the practitioner determines the desired position for the signal delivery devices 110. Optionally, the practitioner may move the partially implanted signal delivery devices 110 without disconnecting the cable assembly 120. Furthermore, in some embodiments, the iterative process of repositioning the signal delivery devices 110 and/or varying the therapy parameters may not be performed.

The signal generator 101, the lead extension 102, the trial stimulator 105 and/or the connector 122 can each include a receiving element 109 or coupler that is configured to facilitate the coupling and decoupling procedure between the signal delivery devices 110, the lead extension 102, the pulse generator 101, the trial stimulator 105 and/or the connector 122. The receiving elements 109 can be at least generally similar in structure and function to those described in U.S. Patent Application Publication No. 2011/0071593, which is herein incorporated by reference in its entirety.

After the signal delivery elements 110 are implanted, the patient 190 can receive therapy via signals generated by the trial stimulator 105, generally for a limited period of time. During this time, the patient wears the cable assembly 120 and the trial stimulator 105 is secured outside the body. Assuming the trial therapy is effective or shows the promise of being effective, the practitioner then replaces the trial stimulator 105 with an implantable signal generator 101, and programs the signal generator 101 with therapy programs that are selected based on the experience gained during the trial period. Optionally, the practitioner can also replace the signal delivery elements 110. Once the implantable signal generator 101 has been positioned within the patient 190, the therapy programs provided by the signal generator 101 can still be updated remotely via a wireless physician's programmer 117 (e.g., a physician's laptop, a physician's remote or remote device, etc.) and/or a wireless patient programmer 106 (e.g., a patient's laptop, patient's remote or remote device, etc.). Generally, the patient 190 has control over fewer parameters than does the practitioner. For example, the capability of the patient programmer 106 may be limited to starting and/or stopping the signal generator 101, and/or adjusting the signal amplitude. The patient programmer 106 may be configured to accept inputs corresponding to pain relief, motor functioning and/or other variables, such as medication use. Accordingly, more generally, the present technology includes receiving patient feedback that is indicative of, or otherwise corresponds to, the patient's response to the signal. Feedback includes, but is not limited to, motor, sensory, and verbal feedback. In response to the patient feedback, one or more signal parameters can be adjusted, such as frequency, pulse width, amplitude or delivery location.

Sterilization

Figure 2:
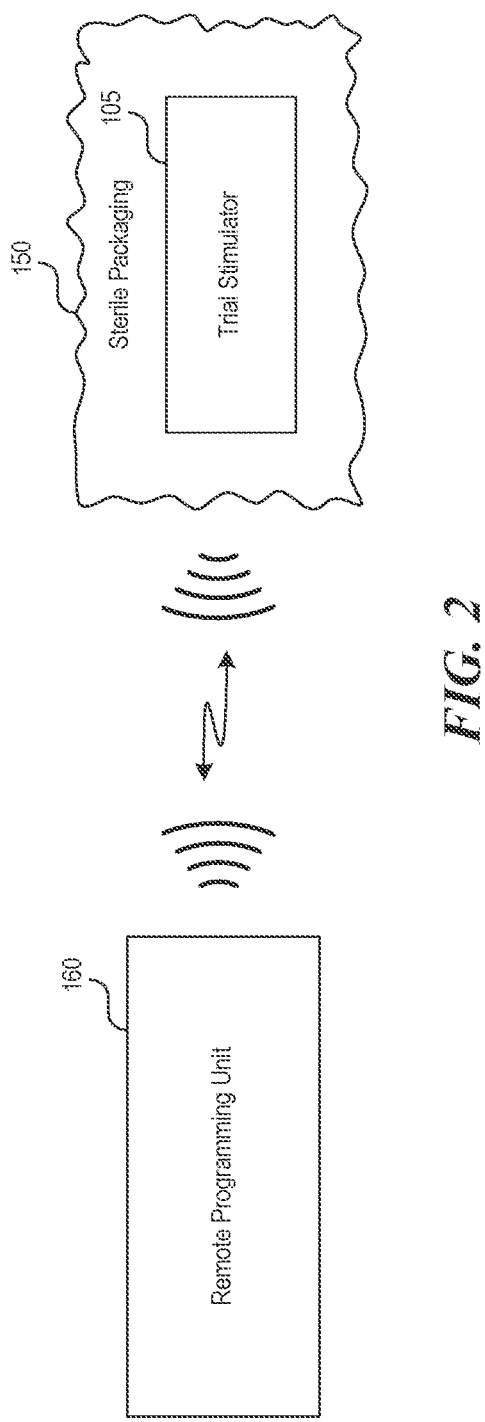
FIG. 2 illustrates a trial stimulator that is placed in a sterile package and that wirelessly communicates with a programming unit in accordance with some embodiments of the disclosed technology.

Because the trial stimulator 105 is connected to the signal delivery devices 110 within a sterile environment, the trial stimulator 105 must itself be sterile prior to use. As shown in FIG. 2, the trial stimulator is preferably stored in a sterile package 150 that is opened just prior to connecting the trial stimulator to the patient. In some embodiments, the sterile package 150 is a pouch that is permeable to sterilizing gasses but impermeable to microbe contaminants (e.g. bacteria, viruses, molds etc.). Suitable pouches are made from Tyvek® or other similar gas-permeable materials.

The most common type of gas used to sterilize medical devices is ethylene oxide (ETO). While this gas is effective for sterilizing equipment, it is also highly flammable. Ethylene oxide can ignite when exposed to an electrical energy discharge as low as 60 micro-joules. Care must be taken to ensure that any electrical circuitry placed in the packaging is completely or nearly completely discharged prior to exposure to the flammable sterilizing gas.

In addition, it is also beneficial if the trial stimulator 105 can be tested prior to its removal from the sterile packaging. Such testing can confirm the functionality of the unit prior to be being brought into a sterile operating theatre. In addition to or in lieu of testing, it may also be desirable to update the trial stimulator firmware and/or other software prior to removing the trial stimulator 105 from the packaging.

Given these implementation targets, an aspect of the presently disclosed technology includes a power control circuit that can be used with a trial stimulator to reduce the amount of energy stored in the trial stimulator to a level that allows the trial stimulator to be safely exposed to (e.g. placed in) a flammable sterilizing gas. In addition, the presently disclosed power control circuit can limit the battery drain of the trial stimulator while the trial stimulator is in a "sleep state" so that the battery remains sufficiently charged to power the circuit. In yet another aspect, the power control circuit can activate or awaken the trial stimulator while it is still in the sterile packaging. These and other aspects of the disclosed technology are discussed in further detail below. Although the power control circuit of the disclosed technology is described with respect to its use with a trial stimulator for nerve stimulation, it will be appreciated that the power control circuit can be used with other electronic devices that are to be stored prior to use and, in particular, with other electronic devices that are to be sterilized in a flammable gas environment.

FIG. 2 shows an environment in which a trial stimulator 105 is stored in a sterile packaging 150. Upon manufacture, the trial stimulator 105 is programmed with firmware required to control the internal circuitry used to deliver stimulation pulses to one or more electrodes in a patient. Once it is confirmed that the trial stimulator 105 is fully functional, it is placed in the packaging 150 and subjected to a sterilizing procedure. In some embodiments, the packaging 150 is a gas-permeable pouch (e.g. formed from Tyvek® or another suitable material) that allows a gas such as ethylene oxide to penetrate into the packaging and sterilize the trial stimulator 105 inside. The gas is withdrawn through the permeable material and the contents of the packaging 150 remains sterile as long as the packaging remains sealed.

Prior to use with a patient, the trial stimulator 105 in the sterile packaging 150 is awakened and begins to communicate with an external device such as a pulse programmer 160. Suitable modes of communication include short distance wireless communication protocols (e.g. Bluetooth, ZigBee, 802.11, infrared and/or other suitable protocols). In some embodiments, the trial stimulator 105 is awakened from a sleep state while still sealed in the sterile packaging 150. The trial stimulator 150 begins wirelessly communicating with the programmer 160 to confirm that the trial stimulator 105 is working and/or to confirm that a battery within the trial stimulator has sufficient power to operate the trial stimulator, and/or to update firmware and/or other stored parameters if necessary. Because the sterilizing gas has been removed from the packaging 150 prior to awakening the trial stimulator, there is no longer a risk of explosion if the trial stimulator is powered up. In some embodiments, the power control circuit draws minimal power from the battery so that the power control circuit is able to keep the trial stimulator in a sleep state for several years without draining the battery to the point that it cannot power the trial stimulator.

Figure 3:
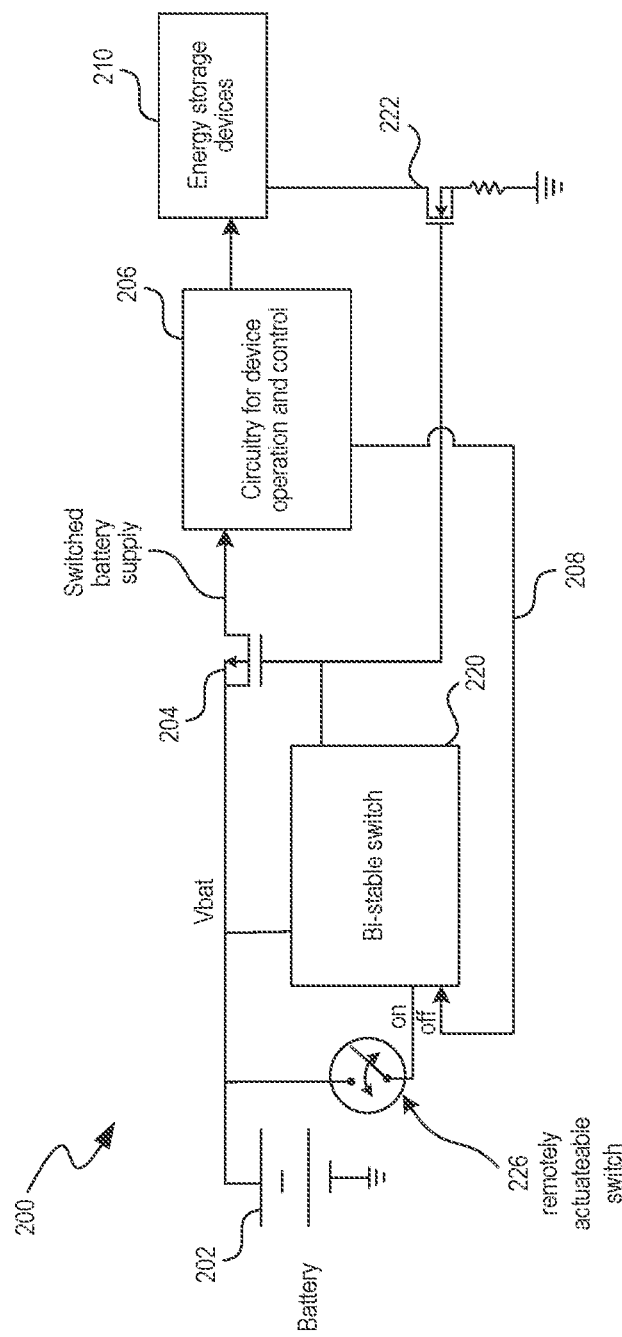
FIG. 3 is a block diagram of a power control circuit for selectively reducing stored energy in a trial stimulator to be sterilized in accordance with some embodiments of the disclosed technology.

FIG. 3 is a block diagram of a power control circuit 200 configured in accordance with some embodiments of the disclosed technology. The power control circuit 200 incudes a power source such as a battery 202 or other energy storage device (e.g. an energy storage capacitor). The battery voltage (Vbat) is connected to the trial stimulator circuitry 206 via an electronically controlled switch (e.g. a transistor) 204. The circuitry 206 includes, among other things, a processor, non-volatile memory for storing instructions or parameters, a radio transceiver for communicating with an external device and/or voltage regulators that produce higher voltages used to deliver the therapeutic pulses to the patient. In addition, the circuitry 206 may include energy storage devices (e.g. capacitors) that store energy in the trial stimulator.

In order to avoid storing enough energy in the trial stimulator to ignite a sterilizing gas, a bi-stable switch 220 controls one or more transistors 204, 222 to put the circuitry of the trial stimulator in a sleep state. In some embodiments, the bi-stable switch 220 puts the trial stimulator in a sleep state by turning off the transistor 204 so that power from the battery does not reach the circuitry 206 in the trial stimulator. In addition, any bus voltage levels and stored energy on the energy storage devices that could potentially ignite a sterilizing gas are drawn down to zero or near zero potential through one or more transistors 222.

In some embodiments, the bi-stable switch 220 operates as a flip flop circuit to produce an output that places the trial stimulator in a run state when battery power is first applied to the switch 220. A processor (not shown) within the trial stimulator circuitry 206 can provide a signal on a line 208 that causes the bi-stable switch 220 to change states and produce a signal that puts the trial stimulator in a sleep state. The signal on line 208 from the processor can be activated once a self-test routine is complete. Alternatively, the processor or other logic circuit can receive a command from an external programmer (not shown) via a wireless connection to put the trial stimulator in a sleep state.

A remotely actuatable switch 226 (e.g. a switch that is actuatable from outside the packaging 150 shown in FIG. 2) is provided to change the state of the bi-stable switch 220 and cause the bi-stable switch to produce a signal causing the connected circuitry to exit the sleep state and enter the run state. The switch 226 can be operated through the sterile packaging so that the trial stimulator need not be removed from the packaging in order to cause the trial stimulator to enter the run state. Suitable remotely actuatable switches include, but are not limited to, magnetically activated reed switches, mechanical switches, pressure activated switches, light activated switches, shock activated switches, and/or Hall-effect switches. In some embodiments, the switch 226 is mechanically operated so that it does not need to be powered while the trial stimulator is in the sleep state.

In some embodiments, the switch 226 is a magnetically activated reed switch. Placing a magnet on the outside of the sterile packaging near the switch 226 closes the reed switch and causes the power control circuit to produce an output that puts the trial stimulator in the run state. More particularly, closing the switch 226 causes the bi-stable switch 200 to generate an output that turns on the transistor 204 and applies the battery voltage to the circuitry 206 within the trial stimulator. In addition, closing the switch 226 turns off the transistor 222 and allows the energy storage devices in the trial stimulator to charge.

Figure 4:
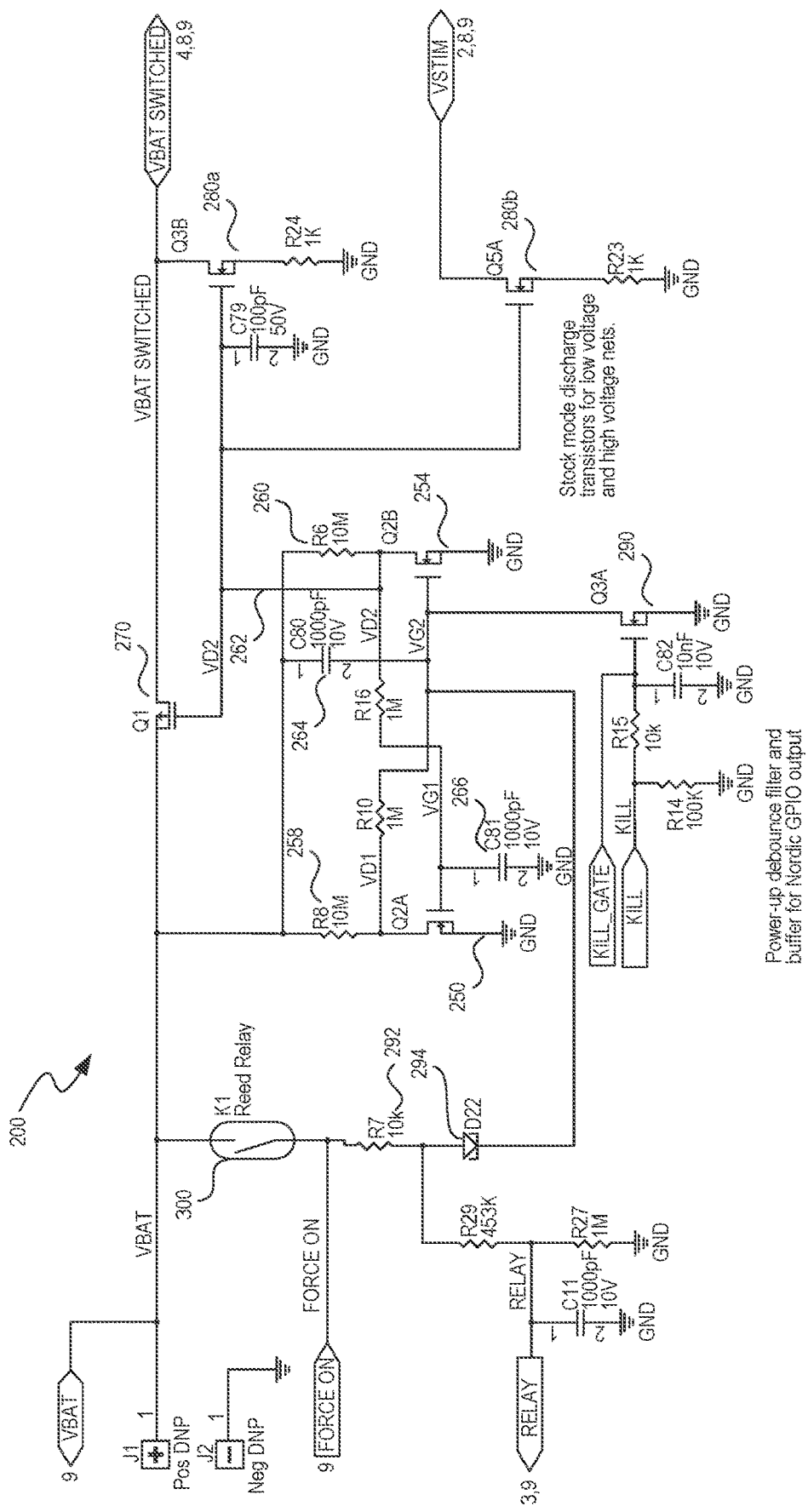
FIG. 4 is a schematic diagram of a power control circuit for selectively reducing stored energy in a trial stimulator to be sterilized in accordance with some embodiments of the disclosed technology.

FIG. 4 is a schematic diagram of a representative embodiment of the power control circuit 200 shown in FIG. 3. The power control circuit 200 includes the bi-stable switch 220 that is configured as a JK flip flop. The flip flop includes two cross-connected FET transistors 250 and 254. Each of the first and second transistors 250, 254 has a source terminal that is grounded. The drain terminal of the first transistor 250 is connected through a first 10 MΩ resistor 258 to the battery voltage Vbat. Similarly, the drain of the second transistor 254 is connected through a second 10 MΩ resistor 260 to the battery voltage Vbat. The node between the drain terminal of the second transistor 254 and the second resistor 260 is connected through a first 1 MΩ resistor to the gate of the first transistor 250. Similarly, the node between the drain of the first transistor 250 and first resistor 258 is connected through a second 1 MΩ resistor to the gate of the second transistor 254. In this way, when the first transistor 250 is turned on, the second transistor 254 is held off. Conversely, when the second transistor 254 is turned on, the first transistor 250 is held off.

In the embodiment shown in FIG. 4, an output 262 of the flip flop circuit that is taken at the node between the drain of the second transistor 254 and the second resistor 260 drives a number of transistors that reduce the energy stored in a connected circuit when the circuit is in a sleep state. As shown, the output 262 feeds a gate of a p-type FET transistor 270 such that when the output 262 is a logic low level, the transistor 270 is turned on and connects the battery power to the connected circuitry 206. In addition, the output 262 is connected to gates of one or more n-type FET transistors 280a, 280b etc. When the output 262 is a logic low level, transistors 280a, 280b are turned off.

When the flip flop changes states, the output 262 goes to a logic high level and the transistor 270 is turned off, thereby disconnecting the battery power from the connected circuitry 206. In addition, the logic high level on output 262 turns the transistors 280a, 280b on. The transistors 280a, 280b are configured to connect any busses and any energy storage devices on the busses or other powered lines to ground through a 1 KΩ resistor so that their voltage is zero or near zero and the energy stored on the capacitors is less than an ignition energy level of a flammable sterilization gas. In some embodiments, the energy stored in the connected circuitry 206 while in the sleep state is reduced to less than 1/10th of that which could ignite a sterilizing gas (e.g. reduced to about 6 uJoules or less for ETO).

With the first transistor 250 conducting and the second transistor 254 in the non-conducting state, the connected circuitry 206 is put into a sleep state. The first and second transistors 250, 254 have a very low leakage current and the 10 MΩ resistors in series with the drain electrodes limits the current of the conducting transistor in the sleep state to a low level (3.6V/10MΩ=360 nA) such that the battery drain is minimal during the sleep state.

In some embodiments, a first 1000 pF capacitor 264 is connected between the battery voltage and the gate of the second transistor 254. Similarly, a second 1000 pF capacitor 266 is connected to the gate of the first transistor 250 and ground. When battery power is first applied to the power control circuit, the first capacitor 264 acts as a short and the battery voltage appears at the gate of the second transistor 254 turning it on and producing a logic low level on the output 262 thereby placing the connected circuitry 206 in a run state. In this way, if a new battery is placed into the circuit, the connected circuitry 206 will immediately begin to operate in the run state. Capacitors 264, 266 also shunt stray EMF signals to ground or the battery and lessen the likelihood that any such EMF will change the state of the flip flop.

The power control circuit 200 will keep the connected circuitry operating in the run state until it is commanded to turn off. In some embodiments, an N-type FET transistor 290 has a drain connected to the gate of the second transistor 254. When the transistor 290 is turned on, the gate of the second transistor 254 is connected to ground and the second transistor 254 is turned off. The output 262 of the power control circuit then goes to a logic high level and the connected circuitry enters the sleep state. In some embodiments, a signal that controls the transistor 290 is received from a processor or other logic circuit in the connected circuitry 206, such that when the circuit completes a self-test or is commanded by an external controller, the processor puts a logic level on the gate of the transistor 290 to take the circuitry out of the run state and put it into the sleep state. A resistor/capacitor combination are connected to the gate of transistor 290 to de-bounce any jitters on the signal applied to the gate of transistor 290.

The power control circuit 200 will continue to produce an output to keep the connected circuitry in the sleep state until the flip flop changes states. In some embodiments, a remotely actuatable switch 300 such as a magnetically activated reed relay is connected between the battery voltage through a 10 KΩ resistor 292 and diode 294 to the gate of the second transistor 254. When the remotely actuatable switch 300 is closed, the battery voltage is applied to the gate of the transistor 254 thereby driving the output 262 to a logic low level and putting the connected circuitry 206 back in the run state. In some embodiments, a resistor divider is connected between the resistor 292 and the in-line diode 294 so that a processor or other logic circuit can detect whether the switch 300 is closed or open depending on the voltage level produced by the resistor divider.

The remotely actuatable switch 300 can be activated from outside of the sterile packaging so that the connected circuitry can be turned on without removing it from the packaging. As indicated above, other types of switches that can be activated through the sterile packaging could also be used such as pressure switches, shock activated switches, light activated switches or even mechanically controlled switches that can be activated through the packaging. A Hall effect switch can also be used, depending on the current draw required to remain powered.

As will be appreciated, the power control circuit 200 operates to selectively apply the battery voltage to connected circuitry in a run state and to bleed or drain energy from energy storage devices in a sleep state. In some embodiments, the power control circuit may leave the battery voltage connected to some circuitry, provided that the current drain is not too great for long periods of storage (e.g. several months to years). However, the power control circuit 200 should drain the energy from the busses/capacitors such that the total energy stored in the circuitry is less than a level that could ignite any sterilizing gas.

From the foregoing, it will be appreciated that specific embodiments of the disclosed technology have been described herein for purposes of illustration, but that various modifications may be made without deviating from the technology. For example, bi-stable switch configurations other than a JK flip flop could be used including D-type flip flops, RS-type flip flops or other logic configurations that are configured to retain a state until directed to change states and that draw little power. In general, any bi-stable switch configuration with the following features could be used: 1) the bi-stable switch state is maintained with a very small amount of power such that the battery is not unduly depleted in long-term storage; 2) the bi-stable switch reliably powers up in a known state, either on or off, when the battery is replaced; 3) the bi-stable switch is tolerant of EMF interference such that it cannot easily be switched by such fields. Any of these switch features might be relaxed in embodiments that do not require them. In addition, the disclosed embodiments can be used with circuitry other than implantable circuitry for treating pain with electrical pulses. For example, the disclosed embodiments can be used with implantable cardiac pacemakers or defibrillators or other implantable or non-implantable electronic devices that require sterilization before use and that store sufficient energy that could ignite a flammable sterilizing gas. Other uses for the disclosed technology include use in treating acute or episodic conditions with neuro-stimulators. These devices require leads that pierce the skin and are generally implanted under sterile conditions. A sterile stimulator with the disclosed power control circuit can make installation and testing of these leads more convenient for the patient and physician.

In some embodiments, the disclosed technology can be used with devices that are to be placed in a sleep state and de-powered to a safe handling level without the need to be placed in an explosive sterilizing environment. For example, circuitry for high voltage power supplies such as the type used in X-ray imaging equipment, ultrasound imaging, MRI devices, cathode ray displays or other vacuum tube-based designs or other devices that produce voltage levels that are potentially dangerous if touched or if they arc. Other representative non-medical devices that can be powered down in a sleep state include circuits for use in rockets or other devices that are sometimes exposed to flammable environments during use or storage. The disclosed circuitry can be used to place such devices in a sleep state until they are to be awakened in an environment where the presence of higher voltages is not dangerous.

Certain aspects of the technology described in the context of particular embodiments may be combined or eliminated in other embodiments. For example, the embodiments described above can be produced without a battery and the battery supplied by an end user prior to sterilization and storage. Further, while advantages associated with certain embodiments of the disclosed technology have been described in the context of those embodiments, other embodiments may also exhibit such advantages, and not all embodiments need necessarily exhibit such advantages to fall within the scope of the present technology. Accordingly, the disclosure and associated technology can encompass other embodiments not expressly shown or described herein.

I claim:

1. A power control circuit configured to selectively place a device into a run state or a sleep state, the power control circuit comprising:
    a flip flop circuit that is configured to produce an output that places a connected device in a run state or a sleep state;
    a transistor that is controlled by the output of the flip flop circuit to drain stored energy from one or more energy storage devices of the connected device when the connected device is in the sleep state; and
    a remotely actuatable switch that is configured to cause the flip flop circuit to produce the output that puts the connected device in the run state without physically touching the switch.

2. The power control circuit of claim 1, wherein the transistor is a first transistor, the power control circuit further comprising a second transistor that is controlled by the output of the flip flop circuit to apply power to the connected device from an energy source while in the run state.

3. The power control circuit of claim 2, further comprising a capacitor connected between the power source and the second transistor such that, upon application of power from the power source to the flip flop circuit, the power turns on the second transistor and produces the output that causes the connected device to operate in the run state.

4. The power control circuit of claim 1, wherein the flip flop circuit comprises a pair of cross-connected transistors, and wherein each of the cross-connected transistors is connected in series with a resistance.

5. The power control circuit of claim 1, wherein the remotely actuatable switch is a magnetically actuated switch.

6. The power control circuit of claim 1, wherein the remotely actuatable switch is a magnetically activated reed switch.

7. The power control circuit of claim 1, wherein the remotely actuatable switch is controllable by light.

8. The power control circuit of claim 1, wherein the remotely actuatable switch is controllable with a shock.

9. The power control circuit of claim 1, wherein the remotely actuatable switch is pressure activated.

10. A power control circuit configured to selectively place a device into a run state or a sleep state, the power control circuit comprising:
a switch configured to produce an output that places a connected device in a run state or a sleep state;
a first transistor controlled by the output of the switch and configured to drain stored energy from the connected device when the connected device is in the sleep state; and
a second transistor controlled by the output of the switch and electrically coupled to the connected device and an energy source, the second transistor being configured to inhibit current flow from the energy source to the connected device when the connected device is in the sleep state.

11. The power control circuit of claim 10, wherein the switch is a bi-stable switch, the power control circuit further comprising a remotely actuatable switch that, when actuated, causes the bi-stable switch to produce the output that puts the connected device in the run state.

12. The power control circuit of claim 10, wherein the switch is a flip flop circuit, and wherein, upon receiving power, the flip flop circuit produces the output that causes circuitry of the connected device to operate in the run state.

13. The power control circuit of claim 10, wherein the switch is a flip flop circuit comprising a pair of cross-connected transistors, and wherein each of the cross-connected transistors is connected in series with a resistance.

14. A method for controlling power to a device having circuitry configured to be placed in a flammable environment before use, the method comprising:
in a power control circuit including a power source, a switch connected to the power source, and a transistor electrically coupled to the power source and circuitry of the device, the transistor being in a first state during which current flow between the power source and the circuitry is inhibited:
receiving a signal at the switch; and
in response to the received signal, producing an output from the switch to cause the transistor to transition to a second state and thereby connect the power source to the circuitry.

15. The method of claim 14, wherein the transistor is a first transistor and the power control circuit further comprises a second transistor connected to the device, wherein the output from the switch causes the second transistor to open and thereby prevent energy from the device from being drained.

16. The method of claim 14, wherein the transistor is a first transistor and the power control circuit further comprises a second transistor connected to the device and configured to prevent the device from storing energy when the device is in the sleep state.

17. The method of claim 14, wherein the output is a first output, the method further comprising producing a second output from the switch to cause the transistor to transition to the first state and disconnect the power source from the circuitry.

18. The method of claim 14, further comprising actuating a remotely actuatable switch positioned between the power source and the switch, causing the signal to be generated.

19. The method of claim 14, further comprising magnetically or optically actuating a remotely actuatable switch, causing the signal to be generated.

20. The method of claim 14, wherein the switch is a flip flop circuit comprising a pair of cross-connected transistors each connected in series with a resistance.

* * * * *

UNITED STATES PATENT AND TRADEMARK OFFICE
CERTIFICATE OF CORRECTION

| | | |
|---|---|---|
| PATENT NO. | : 11,571,570 B2 | |
| APPLICATION NO. | : 17/160223 | |
| DATED | : February 7, 2023 | |
| INVENTOR(S) | : Bret Foreman | |

It is certified that error appears in the above-identified patent and that said Letters Patent is hereby corrected as shown below:

In the Drawings

On sheet 3 of 4, in Figure 3, and on the Title Page, the illustrative print figure, reference Numeral 226, Line 2, delete "actuateable" and insert -- actuatable --.

In the Specification

In Column 6, Line 65, delete "(Vbat)" and insert -- ($V_{bat}$) --.

In Column 7, Line 65, delete "Vbat." and insert -- $V_{bat}$. --.

In Column 7, Line 67, delete "Vbat." and insert -- $V_{bat}$. --.

Signed and Sealed this
Eighteenth Day of July, 2023

Katherine Kelly Vidal
*Director of the United States Patent and Trademark Office*